United States Patent
Fukaya et al.

(10) Patent No.: US 9,913,753 B2
(45) Date of Patent: Mar. 13, 2018

(54) LACRIMAL DUCT TUBE

(71) Applicant: KANEKA CORPORATION, Osaka-shi, Osaka (JP)

(72) Inventors: Kohei Fukaya, Settsu (JP); Hidekazu Miyauchi, Settsu (JP); Mariko Matsumoto, Settsu (JP); Eiji Ogino, Settsu (JP); Chihiro Koga, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 298 days.

(21) Appl. No.: 14/424,882

(22) PCT Filed: Jul. 31, 2013

(86) PCT No.: PCT/JP2013/070798
§ 371 (c)(1),
(2) Date: Feb. 27, 2015

(87) PCT Pub. No.: WO2014/034367
PCT Pub. Date: Mar. 6, 2014

(65) Prior Publication Data
US 2015/0250648 A1    Sep. 10, 2015

(30) Foreign Application Priority Data
Aug. 31, 2012   (JP) ................. 2012-191930

(51) Int. Cl.
*A61M 5/00*    (2006.01)
*A61F 9/007*   (2006.01)
(Continued)

(52) U.S. Cl.
CPC ........ *A61F 9/00772* (2013.01); *A61L 29/041* (2013.01); *A61L 29/049* (2013.01);
(Continued)

(58) Field of Classification Search
CPC .. A61F 9/00772; A61L 29/041; A61L 29/049; A61L 29/06; A61L 29/14; A61L 2430/16
(Continued)

(56) References Cited

U.S. PATENT DOCUMENTS

| 6,858,024 B1 | 2/2005 | Berg et al. |
| 2010/0069882 A1* | 3/2010 | Jennings ........... A61M 25/0138 604/525 |

(Continued)

FOREIGN PATENT DOCUMENTS

| JP | 2000-51363 A | 2/2000 |
| JP | 2001-190681 A | 7/2001 |

(Continued)

OTHER PUBLICATIONS

Machine translation of JP 2001-299924—retrieved from AIPN on Apr. 2, 2017: https://dossier1.j-platpat.inpit.go.jp/tri/all/odse/ODSE_GM101_Top.action.*

(Continued)

*Primary Examiner* — Philip R Wiest
(74) *Attorney, Agent, or Firm* — Birch, Stewart, Kolasch & Birch, LLP

(57) ABSTRACT

The present invention provides a lacrimal duct tube that can be preferably used for the treatment of lacrimal duct obstruction, in particular, sheath guided endoscopic probing having been frequently performed in recent years, the lacrimal duct tube being excellent in passage through a lesion in the lacrimal duct, operability in the lacrimal duct, and manipulation of the endoscope inserted into the lumen of the tube, and providing a sufficient viewing field of the endoscope. The present invention relates to a lacrimal duct tube, including: a pair of tubular members that each has an opening at one end and a hole in a side wall communicating with a lumen; and a connection member that connects other ends of the tubular members, wherein the tubular members each include a plurality of resin portions different in Shore hardness, at least one of the resin portions is positioned between the opening and the hole and forms a lumen wall of (Continued)

the tubular member, and the lumen wall has a Shore hardness of 57D or more.

14 Claims, 11 Drawing Sheets

(51) Int. Cl.
  *A61L 29/04* (2006.01)
  *A61L 29/06* (2006.01)
  *A61L 29/14* (2006.01)
(52) U.S. Cl.
  CPC .............. *A61L 29/06* (2013.01); *A61L 29/14* (2013.01); *A61L 2430/16* (2013.01)
(58) Field of Classification Search
  USPC ....................................................... 604/8–10
  See application file for complete search history.

(56) References Cited

U.S. PATENT DOCUMENTS

| 2012/0215153 A1* | 8/2012 | Fukaya | ............... A61F 9/00772 604/8 |
|---|---|---|---|
| 2015/0018962 A1 | 1/2015 | Matsumoto et al. | |

FOREIGN PATENT DOCUMENTS

| JP | 2001-299924 A | 10/2001 | | |
|---|---|---|---|---|
| JP | 2005-334396 A | 12/2005 | | |
| JP | 2006-507073 A | 3/2006 | | |
| JP | 3792775 B2 | 7/2006 | | |
| JP | 2007-502657 A | 2/2007 | | |
| JP | 2008-36157 A | 2/2008 | | |
| JP | 4164142 B2 | 10/2008 | | |
| JP | 4313110 B2 | 8/2009 | | |
| JP | 2010-213957 A | 9/2010 | | |
| JP | 2012-502743 A | 2/2012 | | |
| WO | WO 2004/047899 A1 | 6/2004 | | |
| WO | WO 2005/021079 A1 | 6/2004 | | |
| WO | WO 2010/033541 A1 | 3/2010 | | |
| WO | WO 2011/049198 | * | 4/2011 | ......... A61F 9/00772 |
| WO | WO 2011/049198 A1 | 4/2011 | | |
| WO | WO 2013/111848 A1 | 8/2013 | | |

OTHER PUBLICATIONS

International Search Report, issued in PCT/JP2013/070798, dated Sep. 3, 2013.

* cited by examiner

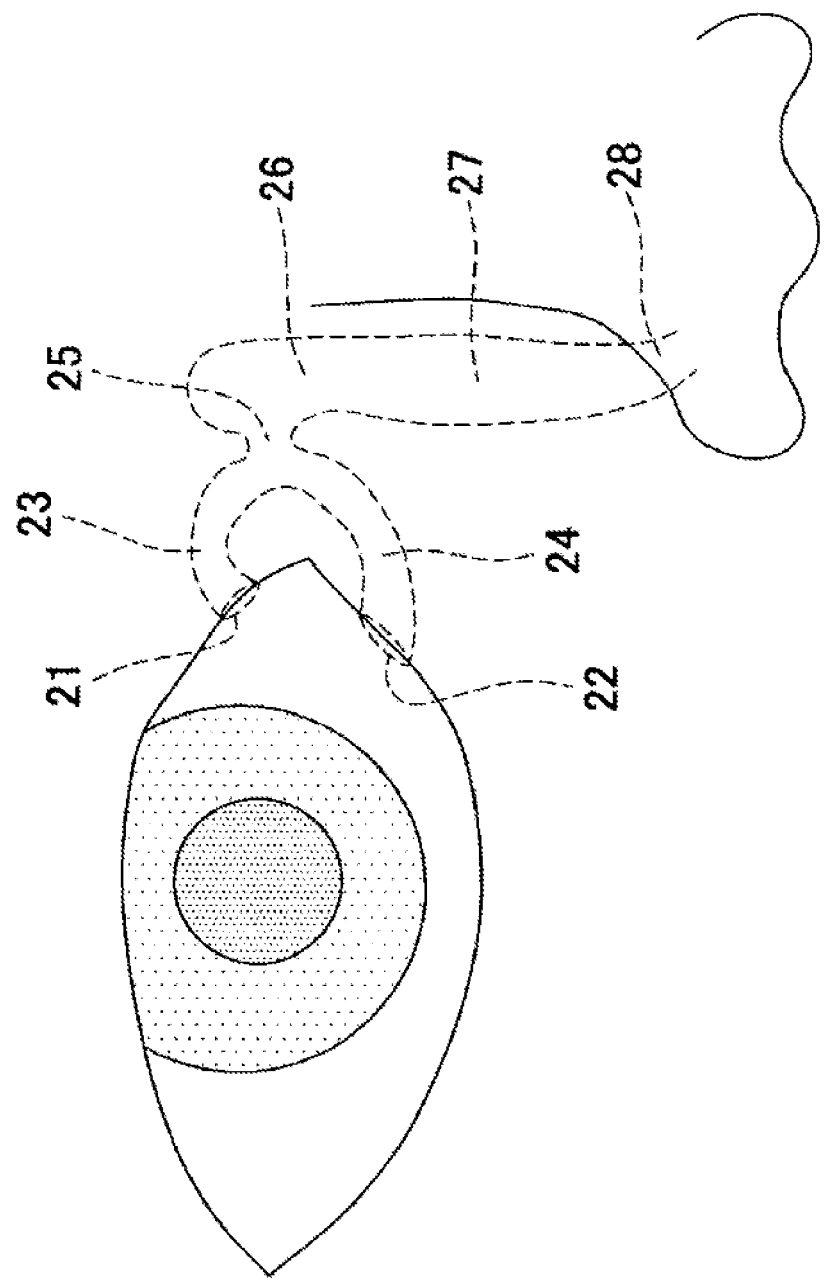
[Fig. 1]

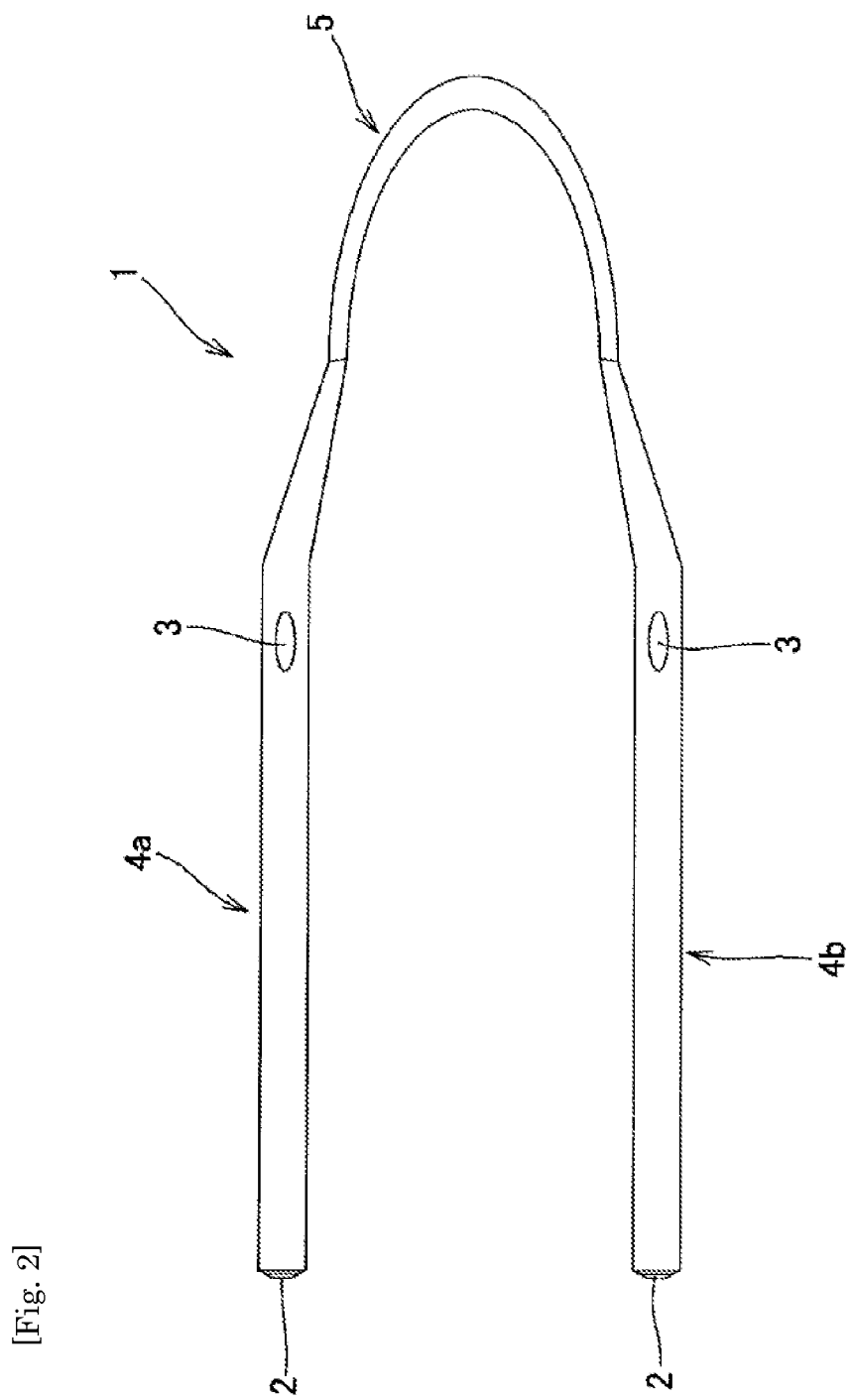
[Fig. 2]

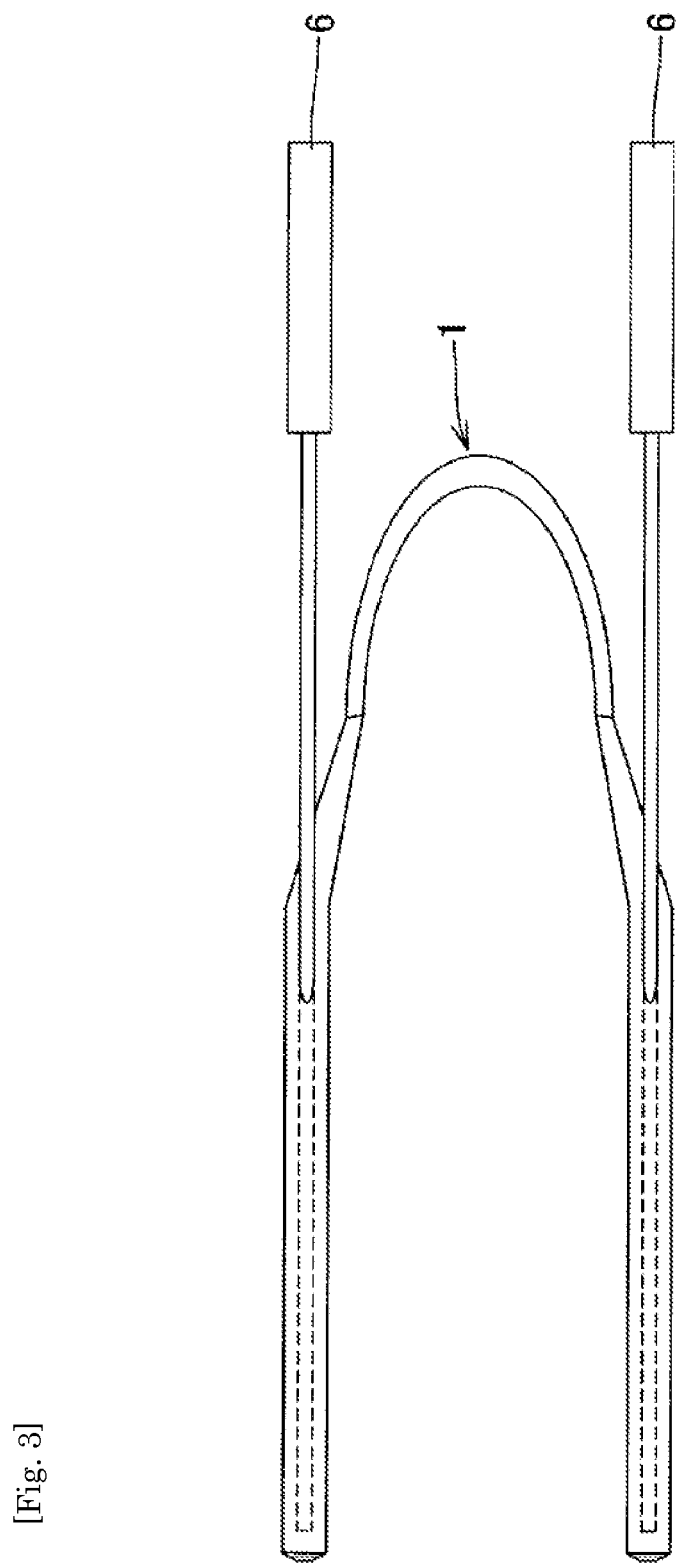
[Fig. 3]

[Fig. 4]
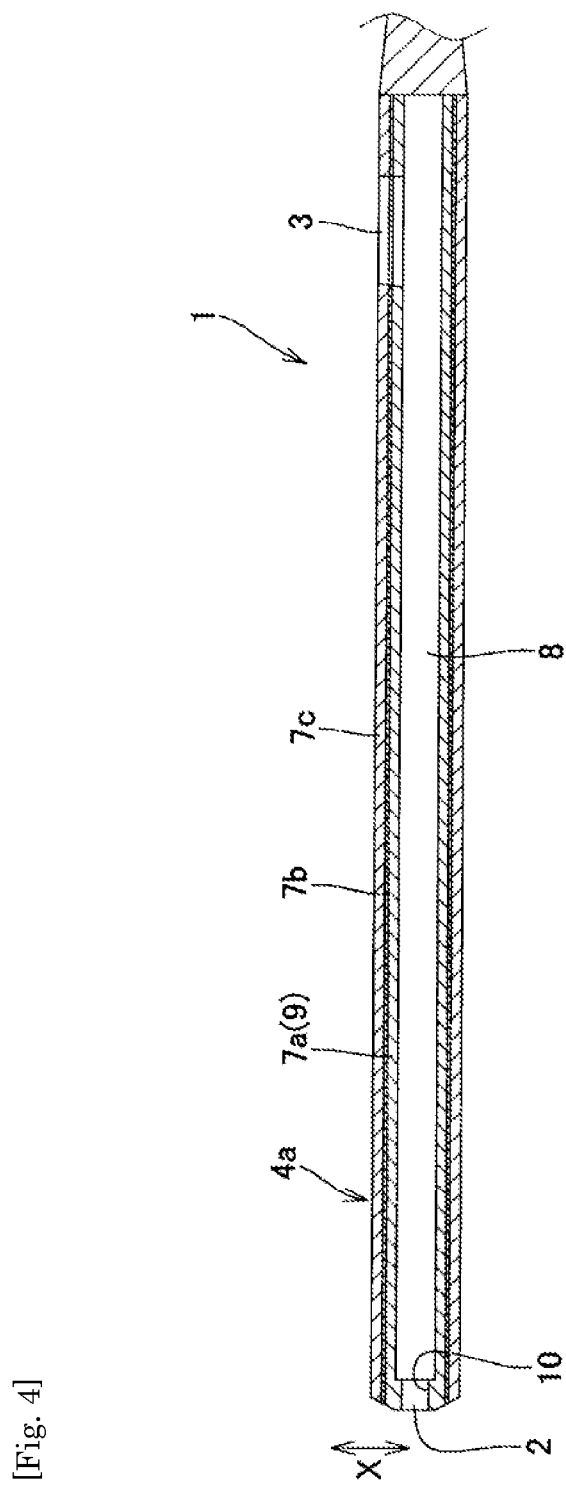

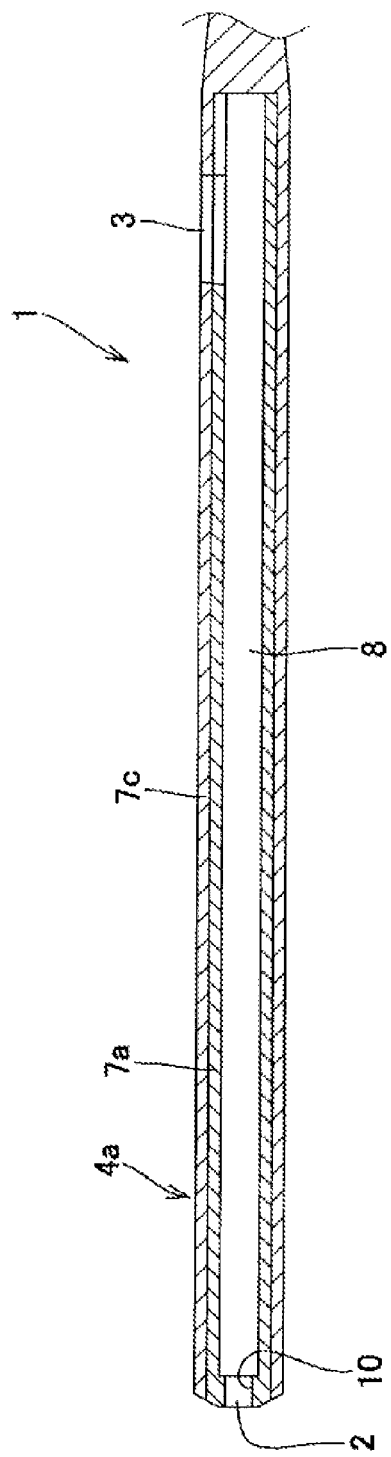
[Fig. 5]

[Fig. 6]
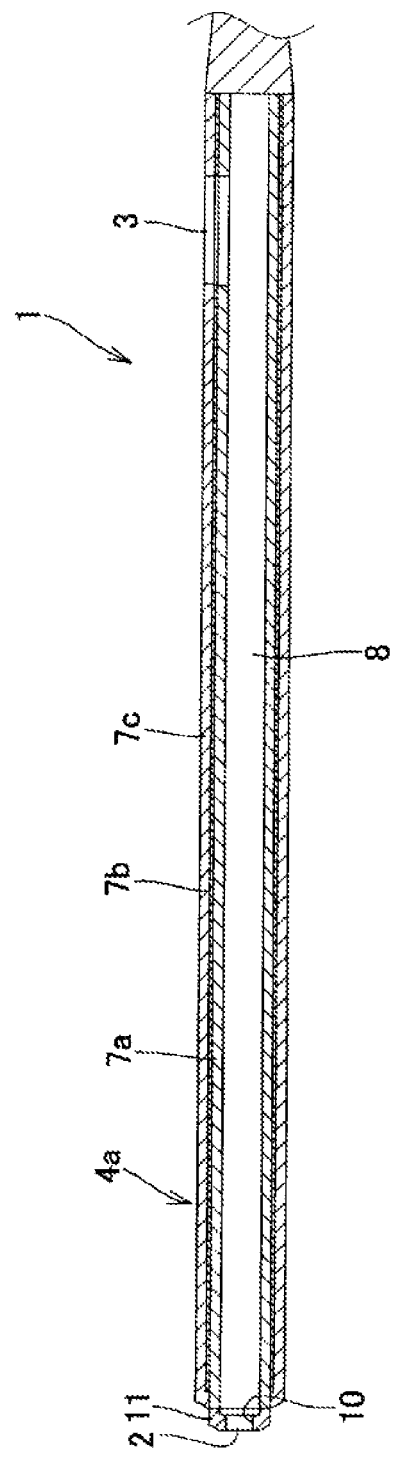

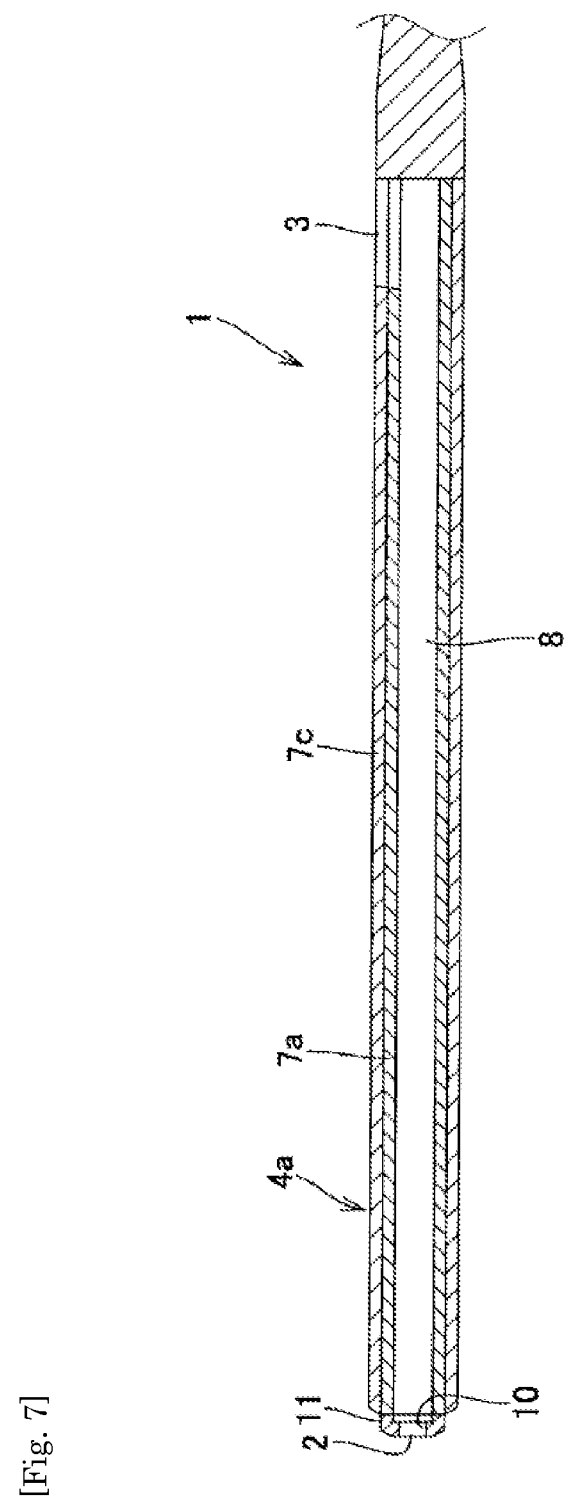
[Fig. 7]

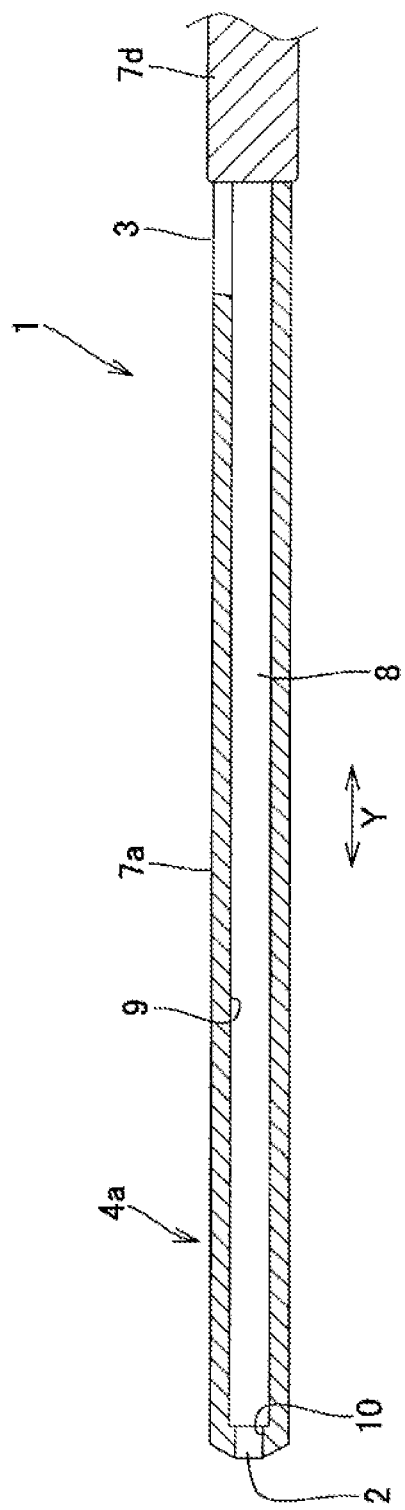
[Fig. 8]

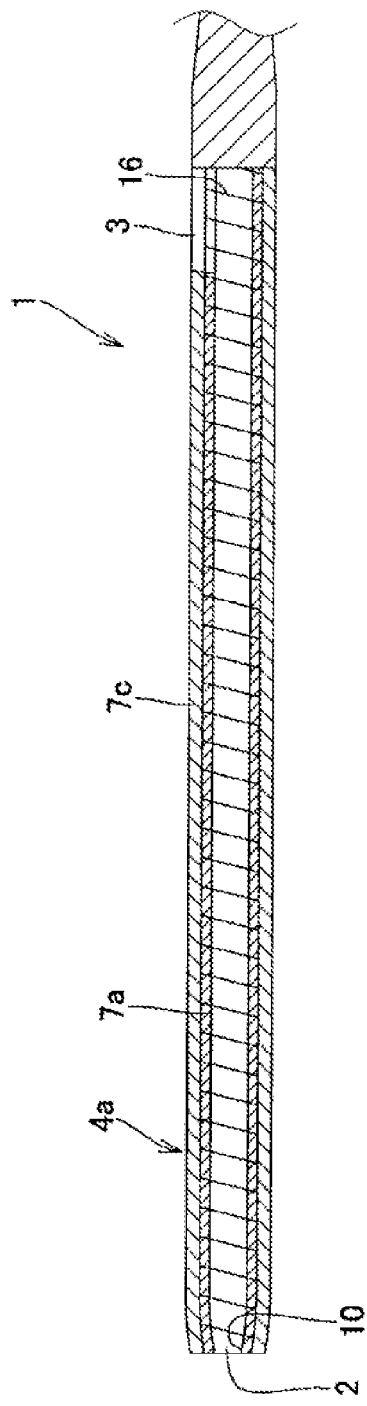
[Fig. 9]

[Fig. 10]
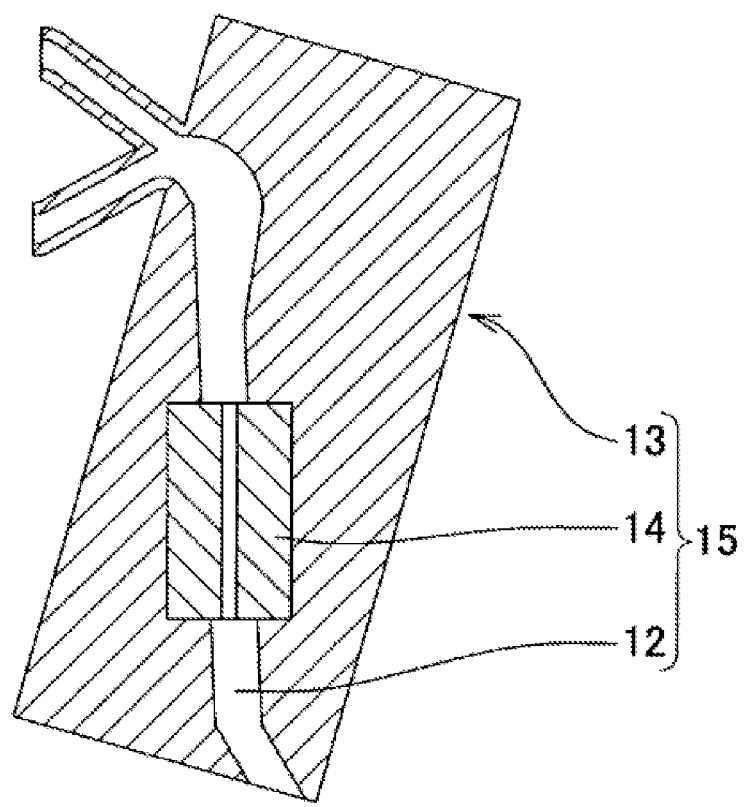

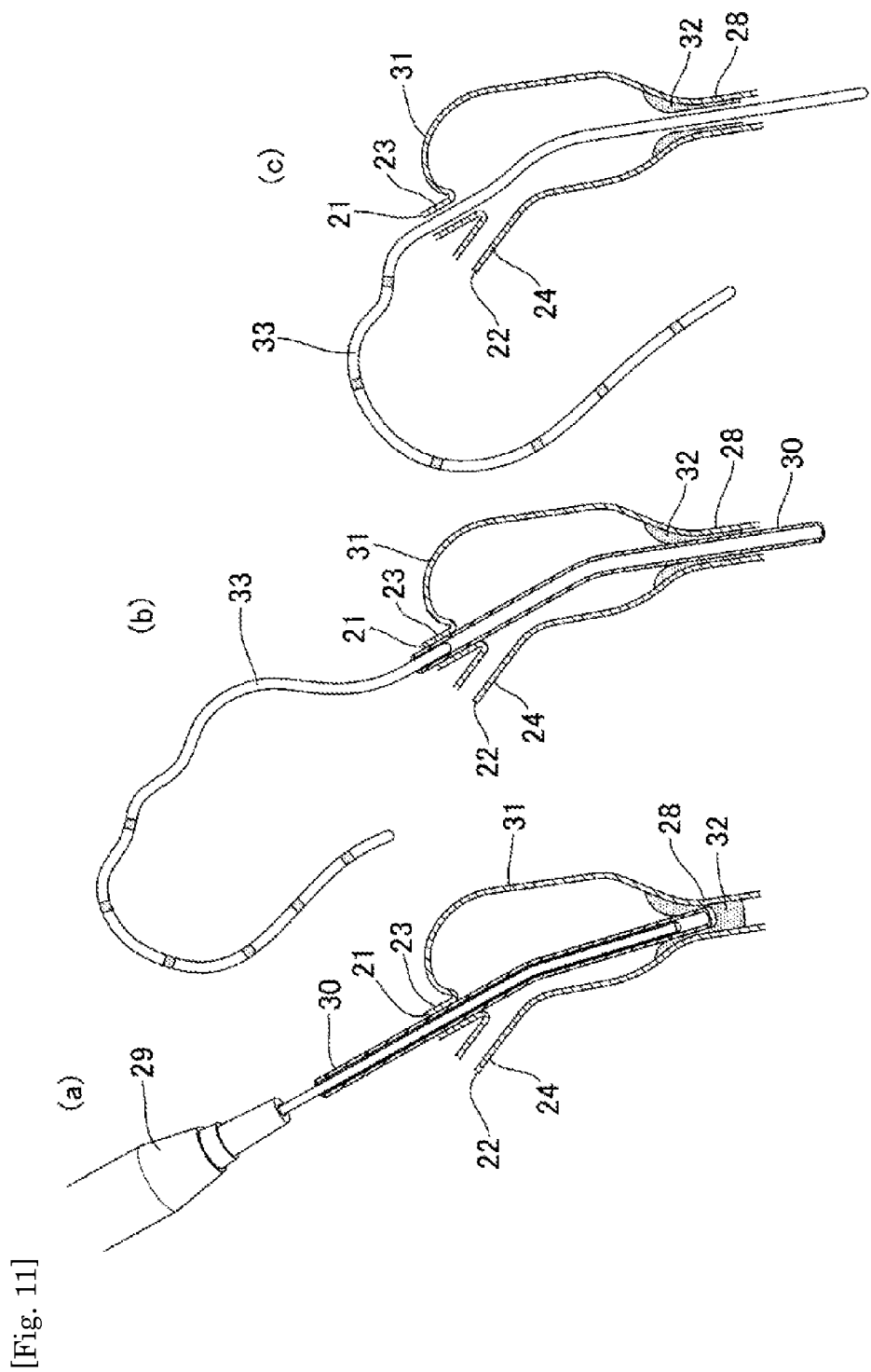
[Fig. 11]

LACRIMAL DUCT TUBE

TECHNICAL FIELD

The present invention relates to a lacrimal duct tube for use in treatment of lacrimal duct obstruction.

BACKGROUND ART

Treatment methods for lacrimal duct obstruction resulting in epiphora include: (i) probing by a lacrimal duct bougie; (ii) placement of a lacrimal duct tube; (iii) dacryocystorhinostomy (DCR); (iv) lacrimal canaliculization; (v) nasolacrimal duct plastic surgery; (vi) lacrimal caruncle moving surgery, and the like.

The probing by a lacrimal duct bougie in (i) is intended to insert a narrow tube called bougie into a lacrimal duct to open an obstructed site and reconstruct a flow path for a lacrimal fluid. This method is conducted as a first treatment in many cases due to its ease of execution and minimal invasiveness. The treatments (iii) dacryocystorhinostomy (DCR), (iv) lacrimal canaliculization, (v) nasolacrimal duct plastic surgery, and (vi) lacrimal caruncle moving surgery are highly effective but relatively invasive because of the need for creation of incisions in a patient's face or drilling holes in bones, and thus are conducted as a last resort.

Lacrimal duct tube for use in the treatment method (ii) is, after the probing by a lacrimal duct bougie (i), placed for maintaining of a flow path and reconstruction of tissues. The placement of a lacrimal duct tube (ii) is easy, less invasive, and highly effective as compared to the foregoing treatment methods (iii) to (vi), and thus is widely performed all over the world. Among such instruments, there is widely available a lacrimal duct tube in which a central part of the tube is formed by a narrow and soft tube or rod and both sides of the tube are formed by hard and thick tubes, as disclosed in Patent Document 1 (for example, refer to FIG. 1).

The lacrimal duct tube includes a tube and a pair of bougies that is inserted from incisions at both sides of the tube, and the bougies are operated to guide the tube into a lacrimal duct and place the tube there. As shown in FIG. 2 of Patent Document 1, a lacrimal duct is formed by lacrimal puncta (21 and 22), lacrimal canaliculi (23 and 24), a lacrimal sac (26), a nasolacrimal duct (27), and others. The lacrimal duct tube is inserted into the lacrimal duct.

However, to insert the lacrimal duct tube, it is necessary to fumble for intra-lacrimal duct operations. The bougies are blindly operated and thus may break through the tube or make a hole at a site other than in the normal lacrimal duct (creating a temporary path), which results in poor therapeutic outcomes. Accordingly, to solve the foregoing problem, the inventor of the present invention has suggested in the past a lacrimal duct intubation instrument in which an opening is formed at the tip of lacrimal duct tube, a reinforcement body is arranged and held in the vicinity of the opening, and the position of the reinforcement body is adjusted within a predetermined distance from the opening (refer to Patent Document 1).

In the recent year's field of lacrimal duct obstruction treatment, surgeries have been newly conducted based on a sheath guided endoscopic probing. At these surgeries, a sheath as an outer casing made of Teflon (registered trademark) or polyurethane covering a lacrimal endoscope was advanced ahead of the lacrimal endoscope in the lacrimal duct to observe from behind that the tip of the sheath opens the obstructed site in the lacrimal duct. This technique is also excellent in allowing exact tube insertion by using the sheath as a guide for tube insertion. Specifically, as shown in FIG. 11(a), a sheath 30 attached to a lacrimal endoscope 29 is inserted into an obstructed site 32 in the inferior nasal meatus 28 of the lacrimal duct 31 from the upper lacrimal punctum 21 through the upper lacrimal canaliculus 23 and passed through the obstructed site 32, and then the lacrimal endoscope 29 is removed. Next, as shown in FIG. 11(b), a lacrimal duct tube 33 is connected to the sheath 30, and the sheath 30 is pulled from the side opposite to the connection side of the lacrimal duct tube 33 to let the lacrimal duct tube 33 pass through the lacrimal duct 31. Then, as shown in FIG. 11(c), the sheath 30 is removed to place the lacrimal duct tube 33 in the lacrimal duct 31.

Next, although not shown, a sheath 30 different from the sheath 30 attached to the lacrimal endoscope 29 is inserted into the obstructed site 32 in the inferior nasal meatus 28 of the lacrimal duct 31 from the lower lacrimal punctum 22 through the lower lacrimal canaliculus 24 into which the lacrimal duct tube 33 is not inserted, and after the sheath 30 is passed through the obstructed site 32, the lacrimal endoscope 29 is removed. Then, an end of the lacrimal duct tube 33 not passing through the obstructed site 32 is connected to the sheath 30, and the sheath 30 is pulled from the side opposite to the connection side of the lacrimal duct tube 33 to let the other end of the lacrimal duct tube 33 pass through the lacrimal duct 31. Finally, the sheath 30 is removed to place the lacrimal duct tube 33 in the lacrimal duct 31.

However, according to the foregoing method, there is the need for a step of connecting the sheath inserted into the patient's lacrimal duct to the lacrimal duct tube. In addition, occurrence of the disconnection may result in an unsuccessful surgery. Thus, there is room for improvement in the method to secure manipulation of the instruments and reduce complexity of the operation.

Meanwhile, instead of using such a sheath, a lacrimal endoscope may be inserted into a lacrimal duct tube. For example, as lacrimal duct tubes usable with a lacrimal endoscope therein, there are known: 1) a lacrimal duct intubation instrument as described in Patent Document 1 that has an opening at the extreme end of a lacrimal duct tube and a reinforcement body arranged and held in the vicinity of the opening, the position of the reinforcement body being adjusted to be at a predetermined distance from the opening; and 2) a lacrimal duct treatment tool including a lacrimal duct placement main body that has an outer diameter allowing insertion into the lacrimal duct and is formed from a flexible material and a sheath part composed of a flexible cylindrical body that is provided at the lower end of the lacrimal duct placement main body and is formed from a harder material than that for the lacrimal duct placement main body (refer to Patent Document 2).

However, in the case of using the sheath guided endoscopic probing, the 1) lacrimal duct intubation instrument has a complicated tube structure, and the reinforcement body cannot be significantly smaller in diameter, and the extreme end of the tube is difficult to harden and thus tends to be slightly weak in pressing force (pushability). In addition, when performing operations with the 1) lacrimal duct intubation instrument, it is necessary to carefully operate the endoscope inserted into the tube because friction between the lacrimal duct tube and the endoscope becomes large.

The 2) lacrimal duct treatment tool is entirely long, which tends to make it difficult to perform smooth operations in general. In addition, it is necessary to separate the lacrimal duct treatment tool main body and the sheath part after placement of the tool in the lacrimal duct.

CITATION LIST

Patent Literatures

Patent Document 1: International Publication WO 2011/049198
Patent Document 2: JP-A No. 2010-213957

SUMMARY OF INVENTION

Technical Problem

In light of the foregoing circumstances, an object of the present invention is to provide a lacrimal duct tube that can be preferably used for the treatment of lacrimal duct obstruction, in particular, sheath guided endoscopic probing having been frequently performed in recent years, more specifically, a lacrimal duct tube that is excellent in passage through a narrowed site or an obstructed site as a lesion in the lacrimal duct, operability in the lacrimal duct, and manipulation of the endoscope inserted into the lumen of the tube, and provides a sufficient viewing field of the endoscope.

Solution to Problem

To solve the foregoing problems, the inventors have earnestly conducted studies and found that it is possible to provide a lacrimal duct tube that is excellent in passage through a lesion in the lacrimal duct, operability in the lacrimal duct, and manipulation of the endoscope inserted into the lumen of the tube, and provides a sufficient viewing field of the endoscope by forming a tubular member constituting the lacrimal duct tube from a plurality of resin portions different in Shore hardness and adjusting the Shore hardness of a lumen wall of the tubular member to a specific hardness, thereby completing the present invention.

Specifically, the gist of the present invention is as follows:

[1] A lacrimal duct tube, including:
a pair of tubular members that each has an opening at one end and a hole in a side wall communicating with a lumen; and
a connection member that connects other ends of the tubular members, wherein
the tubular members each include a plurality of resin portions different in Shore hardness,
at least one of the resin portions is positioned between the opening and the hole and forms a lumen wall of the tubular member, and
the lumen wall has a Shore hardness of 57D or more.

[2] The lacrimal duct tube according to [1], wherein the plurality of resin portions has:
a line structure in which the resin portions are aligned along a longitudinal direction of the tubular member;
a layer structure in which the resin portions are aligned along a thickness direction of the tubular member; or
a mixed structure of the line structure and the layer structure.

[3] The lacrimal duct tube according to [2], wherein the layer structure includes at least one set of layers in which an inner resin portion is higher in hardness than an outer resin portion.

[4] The lacrimal duct tube according to [3], wherein, in the layer structure, the difference in Shore hardness between the inner resin portion and the outer resin portion is 16D or more.

[5] The lacrimal duct tube according to [3] or [4], wherein, in the layer structure, an innermost resin portion is higher in hardness than the other resin portions.

[6] The lacrimal duct tube according to [2], wherein the line structure includes at least one set of lines in which a resin portion on the opening side is higher in hardness than a resin portion on the hole side.

[7] The lacrimal duct tube according to [6], wherein, in the line structure, the difference in Shore hardness between the resin portion on the opening side and the resin portion on the hole side is 16D or more.

[8] The lacrimal duct tube according to [6] or [7], wherein, in the line structure, a resin portion nearest the opening side is higher in hardness than the other resin portions.

[9] The lacrimal duct tube according to any one of [2] to [8], wherein, in the layer structure, the outermost resin portion is formed from polyamide elastomer or a mixed material of polyurethane and SIBS.

[10] The lacrimal duct tube according to any one of [1] to [9], wherein the hole is an inlet for an operating bar or a lacrimal endoscope as a bar-like operative instrument of the lacrimal duct tube.

[11] The lacrimal duct tube according to [10], wherein the lumen wall in the vicinity of the opening has an engagement portion for engagement with a tip of the bar-like operative instrument housed in the lumen through the hole.

[12] The lacrimal duct tube according to [11], wherein the engagement portion forms the diameter of the lumen of the tubular member so as to be smaller than the outer diameter of the tip of the bar-like operative instrument.

[13] The lacrimal duct tube according to any one of [1] to [12], wherein the resin portion having the lumen wall with a Shore hardness of 57D or more is formed from polyamide or polyethylene.

[14] The lacrimal duct tube according to any one of [1] to [13], wherein the lumen wall has a spiral incision.

Advantageous Effects of Invention

According to the lacrimal duct tube of the present invention, the pair of tubular members each has the opening at one end and the hole in the side wall communicating with the lumen. Accordingly, by advancing the tip of the inserted endoscope from the hole to the vicinity of the opening, it is possible to provide a sufficient viewing field of the lacrimal endoscope through the opening, allow the user to surely learn the status of the path through which the tube is passed, and avoid the tube from forming a temporary path and causing damage and bleeding to mucous membranes and the like.

In addition, the tubular members each include the plurality of resin portions different in Shore hardness, and at least one of the resin portions is positioned between the opening and the hole and forms the lumen wall of the tubular member, and the lumen wall has a Shore hardness of 57D or more, which makes it possible to provide the lacrimal duct tube excellent in passage through a lesion in the lacrimal duct, operability in the lacrimal duct, and manipulation of the endoscope inserted into the lumen of the tube.

In the case of the layer structure in which the plurality of resin portions is layered along the thickness direction of the tubular member, when there exists at least one set of layers in which the inner resin portion is higher in hardness than the outer resin portion, it is possible to, when the lacrimal duct tube is used with an endoscope disposed therein, make the extreme end of the tube smaller in diameter and higher in hardness, thereby enhancing the property of passing through the lesion. Accordingly, it is possible to provide a highly operable lacrimal duct tube with improved pushability and decreased friction with the endoscope.

In the layer structure, since the difference of Shore hardness is 16D or more between the inner resin portion and the outer resin portion, it is possible to provide a lacrimal duct tube excellent in retaining a viewing field of the lacrimal endoscope, allowing easy manipulation of the endoscope, and inserting the tube into a lesion such as a narrowed site or an obstructed site in the lacrimal duct.

In the layer structure, the innermost resin portion is higher in hardness than the other resin portions, which makes it possible to further enhance passage through the lesion and reduce friction with the endoscope.

In the case of the line structure in which the plurality of resin portions is aligned along the longitudinal direction of the tubular member, when there exists at least one set of lines in which the opening-side resin portion is higher in hardness than the hole-side resin portion, it is possible to, when the lacrimal duct tube is used with an endoscope disposed therein, make the extreme end of the tube smaller in diameter and higher in hardness, thereby enhancing the property of passing through the lesion. Accordingly, it is possible to provide a highly operable lacrimal duct tube with improved pushability and decreased friction with the endoscope.

In the line structure, since the difference of Shore hardness is 16D or more between the opening-side resin portion and the hole-side resin portion, it is possible to provide a lacrimal duct tube excellent in retaining a viewing field of the lacrimal endoscope, allowing easy manipulation of the endoscope, and inserting the tube into a lesion such as a narrowed site or an obstructed site in the lacrimal duct.

In the line structure, the most opening-side resin portion is higher in hardness than the other resin portions, which makes it possible to further enhance passage through the lesion and reduce friction with the endoscope.

In the layer structure, the outermost resin portion is formed from polyamide elastomer or a mixed material of polyurethane and SIBS, which makes it possible to form the outer layer of the tubular member from the material excellent in flexibility, processability, and biocompatibility.

By using the hole as an inlet for the operating bar as a bar-like operative instrument of the lacrimal duct tube, it is possible to move the lacrimal duct tube to a predetermined position in the lacrimal duct and improve passage through the lesion. In addition, the use of the hole as an inlet for the lacrimal endoscope makes it possible to observe the status in the lacrimal duct.

When the lumen wall in the vicinity of the opening has the engagement portion for engagement with the tip of the bar-like operative instrument stored in the lumen through the hole, the engagement portion acts as a stopper for the bar-like operative instrument inserted into the tubular member. Accordingly, when the lacrimal duct tube is inserted into the lacrimal duct or when the lacrimal duct tube is passed through a lesion such as a narrowed site or an obstructed site, it is possible to prevent the bar-like operative instrument from projecting out of the opening of the tubular member. In addition, since the lacrimal endoscope can be moved up to the vicinity of the opening of the tubular member, it is possible to provide a sufficient viewing field of the endoscope from the opening. Further, by inserting the bar-like operative instrument into the lacrimal duct tube, it is possible to improve the lacrimal duct tube in passage (breaking) through a lesion. In addition, while the lacrimal endoscope is used, it is possible to allow the user to surely learn the status of the path through which the tube is passed, and avoid the tube from forming a temporary path and causing damage and bleeding to mucous membranes and the like.

Since the resin portion having the lumen wall with a Shore hardness of 57D or more is formed from polyamide or polyethylene, it is possible to easily obtain a hardness necessary for passage through the lesion, reduce friction with the endoscope, and facilitate lamination with other materials.

Since the lumen wall has the spiral incision, it is possible to increase the hardness of the lumen wall of the tubular member and improve the manipulation of the endoscope and the flexibility of the tubular member in a balanced manner.

BRIEF DESCRIPTION OF THE DRAWINGS

FIG. 1 is an illustrative diagram of an anatomical structure of a lacrimal duct;

FIG. 2 is a schematic view of one example of a lacrimal duct tube in the present invention;

FIG. 3 is a schematic view of the lacrimal duct tube shown in FIG. 2 in which operating bars as bar-like operative instruments are inserted;

FIG. 4 is a cross-sectional view of a tubular member as one example of the lacrimal duct tube in the present invention;

FIG. 5 is a cross-sectional view of a tubular member as one example of the lacrimal duct tube in the present invention;

FIG. 6 is a cross-sectional view of a tubular member as one example of the lacrimal duct tube in the present invention;

FIG. 7 is a cross-sectional view of a tubular member as one example of the lacrimal duct tube in the present invention;

FIG. 8 is a cross-sectional view of a tubular member as one example of the lacrimal duct tube in the present invention;

FIG. 9 is a cross-sectional view of a tubular member as one example of the lacrimal duct tube in the present invention;

FIG. 10 is a cross-sectional view of a silicon-based lacrimal duct model used in examples; and FIG. 11 is a schematic illustrative diagram showing one example of a surgery of a lacrimal duct obstructed site according to sheath guided endoscopic probing.

DESCRIPTION OF EMBODIMENTS

The present invention will be described below in more detail.

Lacrimal duct referred to in the present invention is a duct (ocular adnexa) composed of upper/lower lacrimal puncta (21/22), upper/lower lacrimal canaliculi (23/24), a common canaliculus (25), a lacrimal sac (26), a nasolacrimal duct (27), a nasal tract (not shown), and Hasner's valve (not shown), as shown in FIG. 1, and configured to guide a lacrimal fluid produced by a lacrimal gland (not shown) from an eye surface to an inferior nasal meatus (28). FIG. 1 shows schematically an anatomical structure of a lacrimal duct. In addition, a duct extending from the upper lacrimal punctum (21) through the upper lacrimal canaliculus (23), and the common canaliculus (25) to the inferior nasal meatus (28) is referred to as an upper lacrimal duct, and a duct extending from the lower lacrimal punctum (22) through the lower lacrimal canaliculus (24), and the common canaliculus (25) to the inferior nasal meatus (28) is referred to as a lower lacrimal duct.

The lacrimal duct tube of the present invention is formed from a tube that is placed in the lacrimal duct, and includes a pair of tubular members each having an opening at one end and a hole in a side wall communicating with the lumen, and a connection member connecting the other ends of the tubular members.

By inserting an endoscope into the tubular members from the holes in the side walls communicating with the lumen up to the vicinity of the openings, it is possible to provide a sufficient viewing field of the endoscope from the openings.

The tubular members include a plurality of resin portions different in Shore hardness.

The Shore hardness here refers to hardness measured by the ASTM2240 method. Similarly, the magnitude of hardness of the lacrimal duct tube in the present invention is determined by Shore hardness.

There is no particular limitation on resin materials for the resin portions. For example, the resin materials may be resin compositions including silicon, polyamide elastomer, polyurethane, isobutylene copolymer, and alloys thereof, but are not limited to them.

In the lacrimal duct tube of the present invention, at least one of the resin portions is positioned between the opening and the hole and forms a lumen wall of the tubular member, and the lumen wall has a Shore hardness of 57D or more.

The Shore hardness of the lumen wall is preferably 70D or more from the viewpoint of favorable passage through a lesion, operability of the tube in the lacrimal duct, and manipulation of the endoscope. In addition, the Shore hardness of the lumen wall is preferably 80D or less and more preferably 75D or less, from the viewpoint of reducing the risk of damaging the lacrimal duct tissues during passage of the tube through the lesion in the lacrimal duct.

Specific structures of the plurality of resin portions different in Shore hardness are as follows:

(1) Line structure in which the resin portions are aligned along the longitudinal direction of the tubular member;

(2) Layer structure in which the resin portions are layered along the thickness direction of the tubular member; and (3) Mixed structure of the line structure and the layer structure.

The number of lines in the line structure and the number of layers in the layer structure may be two each or more. In addition, there are no particular limitations on the entire length of the line structure along the longitudinal direction and the length of each line constituting the line structure as far as these lengths are adjusted within the ranges in which the lines can be used as a lacrimal duct tube. Further, there are no limitations on the thickness of the layers in the layer structure and the diameter of the tube constituting the lines in the line structure as far as the thickness and the diameter are set as appropriate according to the intended use.

The lumen wall here refers to resin portions constituting the lumen.

The lumen wall may have an incision to facilitate bending of the tubular member. By providing a spiral incision in particular, it is possible to increase the hardness of the lumen wall of the tubular member and improve the manipulation of the endoscope and the flexibility of the tubular member in a balanced manner.

According to the present invention, since the layer structure has at least one set of layers in which the inner resin portion is higher in hardness (Shore hardness of 57D or more) than the outer resin portion, it is possible to, when the lacrimal duct tube is used with an endoscope disposed therein, make the extreme end of the tube smaller in diameter and higher in hardness, thereby enhancing the property of passing through the lesion. Accordingly, it is possible to provide a highly operable lacrimal duct tube with improved pushability and decreased friction with the endoscope.

Above all, in the layer structure, by adjusting the difference in Shore hardness between the inner resin portion and the outer resin portion to 16D or more, it is possible to favorably retain the viewing field of the lacrimal endoscope, improve the manipulation of the endoscope, and facilitate the insertion of the tube into a lesion such as a narrowed site or an obstructed site in the lacrimal duct. The difference in Shore hardness is more preferably 20D or more and further preferably 25D or more.

In addition, the upper limit of the difference in Shore hardness may be 50D or less, although it cannot be completely defined depending on the Shore hardness of the innermost resin portion.

In particular, since the innermost resin portion is higher in hardness than the other resin portions in the layer structure, it is possible to further facilitate the passage of the tube through the lesion and reduce friction with the endoscope. For example, when an intermediate layer is interposed between the innermost resin portion and the outermost resin portion, it is preferred that the innermost resin portion is higher in hardness than the resin portion in the intermediate layer and the outermost resin portion. In addition, it is preferred that the resin portion in the intermediate layer is higher in hardness than the outermost resin portion.

When two or more intermediate layers are provided, it is preferred that the resin portions in the intermediate layer become higher in hardness from the outer side to the inner side in a stepwise manner.

According to the present invention, in the layer structure, the outermost resin portion of the tubular member is formed from polyamide elastomer or a mixed material of polyurethane and styrene-isobutylene-styrene block copolymer (SIBS), which produces an advantage in that the outer layer of the tubular member can be formed from the material excellent in flexibility, processability, and biocompatibility.

In the case of the resin formed from polyurethane and SIBS, the hardness of the resin portions can be adjusted by changing the ratio between polyurethane and SIBS. For example, by increasing the proportion of polyurethane, the resin portions can be made higher in hardness. From the viewpoint of flexibility, the weight ratio between polyurethane and SIBS is preferably 1/99 to 99/1. The resin portions may be formed only from polyurethane and SIBS or may contain a mixture of other resin components.

Preferred as the polyurethane are "Miractran E385PNAT" produced by Nippon Miractran Co., Ltd. and "Tekotan TT1074A" produced by Noveon Inc., which are ether aromatic cyclic polyurethanes, or "Tecoflex EG100A" and "Tecoflex EG85A" produced by Noveon Inc., which are ether cycloaliphatic polyurethanes, or "Karubotan PC3575A" produced by Noveon Inc., which is a polycarbonate-based polyurethane.

As the SIBS, "SIBSTAR102T" produced by Kaneka Corporation is more preferred.

The resin portion having the lumen wall with a Shore hardness of 57D or more is formed from polyamide or polyethylene, which produces advantages in that it is possible to easily obtain hardness required for passage of the tube through a lesion, reduce friction with the endoscope, and facilitate lamination with other materials.

In addition, since the line structure has at least one set of lines in which the opening-side resin portion is higher in hardness (Shore hardness of 57D or more) than the hole-side resin portion, it is possible to, when the lacrimal duct tube is used with an endoscope disposed therein, make the extreme end of the tube smaller in diameter and higher in hardness, thereby enhancing the property of passing through the lesion. Accordingly, it is possible to provide a highly operable lacrimal duct tube with improved pushability and decreased friction with the endoscope.

Above all, in the line structure, by adjusting the difference in Shore hardness between the opening-side resin portion and the hole-side resin portion to 16D or more, it is possible to favorably retain the viewing field of the lacrimal endoscope, improve the manipulation of the endoscope, and facilitate the insertion of the tube into a lesion such as a narrowed site or an obstructed site in the lacrimal duct. The difference in Shore hardness is more preferably 30D or more. The upper limit of the difference in Shore hardness may be 50D or less, although it cannot be completely defined depending on the Shore hardness of the most opening-side resin portion.

In particular, since the most opening-side resin portion is higher in hardness than the other resin portions in the line structure, it is possible to further facilitate the passage of the tube through the lesion and reduce friction with the endoscope.

In the lacrimal duct tube of the present invention, the hole is an inlet for a bar-like operative instrument of the lacrimal duct tube such as an operating bar or a lacrimal endoscope.

There is no particular limitation on the size of the hole as far as a bar operative instrument such as the operating bar or the lacrimal endoscope can be inserted into the hole. However, the hole is preferably of a certain size because tears flows between the hole and the end opening. In addition, there is no particular limitation on the shape of the hole but the hole may be circular, oval, square, or polygonal in shape. However, the shape of the hole may be preferably oval to reduce friction with the endoscope.

There is no particular limitation on the operating bar and the lacrimal endoscope as far as they can be used for treatment of lacrimal duct obstruction.

The lumen wall in the vicinity of the opening may have the engagement portion for engagement with the tip of the bar-like operative instrument stored in the lumen through the hole.

In the present invention, the engagement portion specifically refers to a portion that forms the diameter of the lumen of the tubular member so as to be smaller than the outer diameter of the tip of the bar-like operative instrument.

By forming the engagement portion, the engagement portion acts as a stopper for the bar-like operative instrument inserted into the tubular member. Accordingly, when the lacrimal duct tube is inserted into the lacrimal duct or when the lacrimal duct tube is passed through a lesion such as a narrowed site or an obstructed site, it is possible to prevent the bar-like operative instrument from projecting out of the opening of the tubular member. In addition, since the lacrimal endoscope can be moved up to the vicinity of the opening of the tubular member, it is possible to provide a sufficient viewing field of the endoscope from the opening. Further, by inserting the bar-like operative instrument into the lacrimal duct tube, it is possible to improve the lacrimal duct tube in passage (breaking) through a lesion. In addition, while the lacrimal endoscope is used, it is possible to allow the user to surely learn the status of the path through which the tube is passed, and avoid the tube from forming a temporary path and causing damage and bleeding to mucous membranes and the like.

The engagement portion can be formed by decreasing the inner diameter of the tip of the tubular member through thermal processing on a core material with a predetermined outer diameter. Alternatively, the inner diameter may be decreased by connecting another tubular member to the tip of the tubular member constituting the lacrimal duct tube in the present invention.

There is no particular limitation on the shape of the engagement portion as far as it can lock the bar-like operative instrument. For example, the cross-sectional shape of the tubular member along the thickness direction may be a circle, a partly chipped circle, or a circle with at least one projection toward the lumen.

The inner diameter of the tubular member at the engagement portion needs to be smaller than the diameter of the bar-like operative instrument. From the viewpoint of providing a sufficient viewing field of the lacrimal endoscope, the inner diameter of the tubular member at the engagement portion is preferably 0.50 to 0.90 mm and more preferably 0.65 to 0.86 mm.

The engagement portion is positioned in the vicinity of the opening and at a predetermined distance from the opening. The predetermined distance is decided from the viewpoints of acting as a stopper for the lacrimal endoscope and providing a sufficient viewing field of the lacrimal endoscope. For example, from the viewpoint of providing a sufficient viewing field of the lacrimal endoscope, the lens at the tip of the lacrimal endoscope is positioned within 2 mm from the most extreme end of the tube opening. From the viewpoint of providing a viewing field of 70% or more of the lacrimal endoscope, the lens at the tip of the lacrimal endoscope is positioned preferably within 1.5 mm and more preferably within 1 mm, from the most extreme end of the tube opening. Therefore, from the viewpoint of providing a sufficient viewing field of the lacrimal endoscope, the predetermined distance is preferably within 2 mm, more preferably within 1.5 mm, and further preferably within 1 mm from the opening (most extreme end of the opening).

The axial length of the tubular member at the engagement portion needs to allow locking of a bar-like operative instrument such as a lacrimal endoscope and provide a sufficient viewing field of the lacrimal endoscope. For example, the axial length of the tubular member at the engagement portion may fall within a range of 0.3 to 2 mm.

To enhance the insertability of the lacrimal duct tube into the lacrimal duct, the outside of the tubular member may be coated with a hydrophilic coating. The coating develops the lubricity of the lacrimal duct tube in contact with the blood to reduce resistance at the time of insertion of the tube. Although there is no particular limitation on the kind of the hydrophilic coating, the coating is preferably formed from a hydrophilic polymer such as poly(2-hydroxyethyl methacrylate), polyacrylamide, polyvinylpyrrolidone, or polyethyleneglycol, or a blended material thereof.

A plurality of embodiments of the lacrimal duct tube according to the present invention will be described below with reference to the accompanying drawings. However, the present invention is not limited to these embodiments.

FIG. 2 shows one example of an outer appearance of a lacrimal duct tube 1 in the present invention. The lacrimal duct tube 1 includes: a pair of tubular members 4*a* and 4*b* that each have an opening 2 at one end and a hole 3 in a side wall communicating with the lumen; and a connection member 5 that connects other ends of the tubular members 4*a* and 4*b*.

In the lacrimal duct tube 1 of the embodiment, the tubular members 4a and 4b are connected to the connection member 5 that is thinner than the tubular members 4a and 4b.

In the case of connecting outer resin materials of the tubular members 4a and 4b to the connection member 5, the ends of the tubular members 4a and 4b on the sides opposite to the openings 2 are reduced in diameter and closed such that the outer resin materials are arranged at the extreme ends, and then are welded to the connection member 5. In the case of connecting inner resin materials of the tubular members 4a and 4b to the connection member 5, the ends of the connection member 5 are inserted into the lumens of the tubular members 4a and 4b on the sides opposite to the openings 2, and then the tubular members 4a and 4b and the connection member 5 are heated and welded together according to a common procedure.

FIG. 3 shows the state that bar-like operative instruments (operating bars) 6 are inserted into the lacrimal duct tube 1 from the holes 3 shown in FIG. 2. The holes 3 shown in FIGS. 2 and 3 are oval in shape, but the shape of the holes 3 may be a circle, square, or polygon or an incision of a size that allows easy insertion of the bar-like operative instruments 6.

FIG. 4 is a schematic cross-sectional view of a tubular member 4a as one embodiment of the lacrimal duct tube 1 in the present invention. In the tubular member 4a, three layers of resin portions 7a (inner layer), 7b (intermediate layer), and 7c (outer layer) are laminated along a thickness direction X of the tubular member between the opening 2 and the hole 3. The inner space at the innermost resin portion 7a forms a lumen 8 and the resin portion 7a constitutes a lumen wall 9. In the lacrimal duct tube 1 shown in FIG. 4, the inner resin portion 7a is preferably higher in hardness than the outer resin portions 7b and 7c in the layer structure. There is no particular limitation on the difference in hardness between the resin portion 7b and the resin portion 7c. Therefore, in the lacrimal duct tube 1 of FIG. 4, there is only one set of the layers in which the inner resin portion is higher in hardness than the outer resin portions, and there is only one set of lines aligned along the longitudinal direction.

The resin portion 7a has a Shore hardness of 57D or more (the same thing can be applied to following descriptions with reference to the subsequent diagrams).

An engagement portion 10 is formed near the opening 2 of the lacrimal duct tube 1 shown in FIG. 4. The engagement portion 10 engages with the tip of the bar-like operative instrument 6 stored in the lumen 8 as shown in FIG. 3 to prevent the tip of the bar-like operative instrument 6 from protruding out of the opening 2.

FIG. 5 shows one embodiment of the lacrimal duct tube 1 in the present invention, which is basically the same as the lacrimal duct tube shown in FIG. 4 except that two-layer tubular member 4a without the resin portion 7b as an intermediate layer is employed.

FIG. 6 shows one embodiment of the lacrimal duct tube 1 in the present invention, and is basically the same as the lacrimal duct tube shown in FIG. 4 except that another tubular member 11 is connected to the tip of the tubular member 4a and the engagement portion 10 is formed at the tubular member 11. The other tubular member 11 will be also referred to as a chip, and its inner diameter may be the same as that of the tubular member 4a or may be smaller than that of the same.

In the lacrimal duct tube 1 of FIG. 6, the resin portion 7a constituting the inner layer is arranged from the opening 2 to the vicinity of the hole 3, and the resin portion 7c is arranged from the vicinity of the hole 3 to the other end as a portion of connection with the connection member 5. Therefore, in the lacrimal duct tube 1 of FIG. 6, the layer in which the inner resin portion is higher in hardness than the outer resin portions and the layer composed of a single resin portion are connected together to produce two sets of longitudinal lines, thereby forming a mixed structure of a line structure and a layer structure.

FIG. 7 shows one embodiment of the lacrimal duct tube 1 in the present invention, which is basically the same as the lacrimal duct tube shown in FIG. 6 except that a two-layer tubular member 4a without the resin portion 7b as an intermediate layer is employed.

FIG. 8 shows one embodiment of the lacrimal duct tube 1 in the present invention, which has a line structure in which resin portions 7a and 7d are aligned along a longitudinal direction Y of the tubular member 4a. In the tubular member 4a, the resin portion 7a ranges from the opening 2 to the hole 3, and the resin portion 7d ranges from the hole 3 to the other end as a portion of connection with the connection member 5. In this case, in the line structure, the resin portion 7a nearest the opening 2 is adjusted to be higher in hardness than the resin portion 7d. The resin portion 7a constitutes a lumen wall 9.

An engagement portion 10 is formed in the vicinity of the opening 2 in the tubular member 4a.

FIG. 9 shows one embodiment of the lacrimal duct tube 1 in the present invention, which has a spiral incision 16 in the resin portion 7a as an inner layer. The resin portion 7a is arranged from the opening 2 to the hole 3, and the resin portion 7c is laminated to the outside of the resin portion 7a. In addition, the resin portion 7c ranges from the hole 3 to the other end as a portion of connection with the connection member 5.

The lacrimal duct tube in the present invention can be preferably used in treatment of lacrimal duct obstruction, in particular, sheath guided endoscopic probing having been frequently performed in recent years. As a usage example, instead of the sheath 30 shown in FIG. 11(*a*), the tip of the lacrimal endoscope 29 is inserted into the hole 3 of the lacrimal duct tube 1 in the present invention. The lacrimal duct tube 1 in the present invention can provide a sufficient viewing field of the lacrimal endoscope 29 from the tip as described above. Since the present invention enhances operability of the tube in the lacrimal duct and secure manipulation of the endoscope inserted in the lumen of the tube, the user can easily identify a lesion such as the obstructed site 32 while observing the inside of the lacrimal duct 31 from the tip of the lacrimal duct tube 1 through the use of the lacrimal endoscope 29. In addition, since the lacrimal duct tube 1 in the present invention is excellent in passage through a narrowed site or an obstructed site as a lesion in the lacrimal duct, the user can easily thrust the tip of the lacrimal duct tube 1 into the identified lesion and allow the tip of the lacrimal duct tube 1 to penetrate through the same.

In conventional sheath guided endoscopic probing, as shown in FIGS. 11(*b*) and 11(*c*), the sheath 30 is caused to penetrate through the obstructed site 32 and the lacrimal duct tube 33 is connected to the sheath 30, and then the sheath 30 is pulled out to place the lacrimal duct tube 30 in the lacrimal duct. In contrast, when the lacrimal duct tube 1 in the present invention is used, the lacrimal duct tube 1 can be attached to the lacrimal endoscope without the use of a sheath to penetrate directly the lesion in the lacrimal duct and can be placed in the lacrimal duct. This makes it possible to perform surgical operations in a simpler manner than the conventional method.

EXAMPLES

Example 1

Three-layer tubes with an outer diameter of 1.35 mm and an inner diameter of 0.95 mm were formed by multi-layer extrusion using an extruder such that a layer structure included: an inner layer with a cross-sectional thickness of 0.050 mm that was composed of high-density polyethylene with a Shore hardness of 72D (HB530 produced by Japan Polyethylene Corporation, the same thing can be applied to the high-density polyethylene with a Shore hardness of 72D described below); an intermediate layer with a cross-sectional thickness of 0.010 mm that was composed of a low-density polyethylene with a Shore hardness of 50D (PX3080 produced by Equistar Chemicals, the same thing can be applied to the low-density polyethylene with a Shore hardness of 50D described below); and an outer layer with a cross-sectional thickness of 0.140 mm that was composed of a mixture with a Shore hardness of 30D of polyurethane with a Shore hardness of 30D (Tecoflex EG85A produced by Noveon Inc., the same thing can be applied to the polyurethane with a Shore hardness of 30D described below) and SIBS (SIBSTAR (registered trademark) 102T produced by Kaneka Corporation, the same thing can be applied to the SIBS described below).

Cylindrical member with an outer diameter of 0.70 mm was formed from a mixture of polyurethane with a Shore hardness of 30D and SIBS using an extruder.

The 40-mm three-layer tubes were arranged as tubular members on both sides. Then, the 25-mm cylindrical member was set as an intermediate connection member. The ends of the connection member were inserted into the lumens of the tubular members and the resin portions were welded together. After that, the tips of the tubular members were thermally compressed and bonded to core materials with an outer diameter of 0.86 mm using a shrink tube to form engagement portions (0.5 mm long) with an inner diameter reduced to 0.86 mm. In addition, holes were formed in the side surfaces of the tubular members at positions of 30 mm from the both ends, thereby completing a lacrimal duct tube as shown in FIG. 4.

Example 2

Two-layer tubes with an outer diameter of 1.31 mm and an inner diameter of 0.95 mm were formed by multi-layer extrusion using an extruder such that a layer structure included: an inner layer with a cross-sectional thickness of 0.080 mm that was composed of nylon 12 with a Shore hardness of 72D (Rilsan (registered trademark) produced by Arkema Inc., the same thing can be applied to the nylon 12 described below); and an outer layer with a cross-sectional thickness of 0.100 mm that was composed of polyamide elastomer with a Shore hardness of 40D (Pebax (registered trademark) 4033 produced by Arkema Inc., the same thing can be applied to the polyamide elastomer with a Shore hardness of 40D described below).

Cylindrical member with an outer diameter of 0.70 mm was formed from polyamide elastomer with a Shore hardness of 40D using an extruder.

The 40-mm two-layer tubes were arranged as tubular members on both sides. Then, the 25-mm cylindrical member was set as an intermediate connection member. The polyamide elastomers in the tubular members and the connection member were welded together. After that, the tips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the both ends, thereby completing a lacrimal duct tube as shown in FIG. 5.

Example 3

Two-layer tubes with an outer diameter of 1.31 mm and an inner diameter of 0.95 mm were formed by multi-layer extrusion using an extruder such that a layer structure included: an inner layer with a cross-sectional thickness of 0.080 mm that was composed of polyamide elastomer with a Shore hardness of 72D (Pebax (registered trademark) 7233 produced by Arkema Inc.); and an outer layer with a cross-sectional thickness of 0.100 mm that was composed of polyamide elastomer with a Shore hardness of 40D.

Cylindrical member with an outer diameter of 0.70 mm was formed from polyamide elastomer with a Shore hardness of 40D using an extruder.

The 40-mm two-layer tubes were arranged as tubular members on both sides. Then, the 25-mm cylindrical member was set as an intermediate connection member. The polyamide elastomers in the tubular members and the connection member were welded together. After that, the tips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the both ends, thereby completing a lacrimal duct tube as shown in FIG. 5.

Example 4

Two-layer tubes with an outer diameter of 1.35 mm and an inner diameter of 0.95 mm were formed by multi-layer extrusion using an extruder such that a layer structure included: an inner layer with a cross-sectional thickness of 0.100 mm that was composed of linear low-density polyethylene with a Shore hardness of 57D (UF421 produced by Japan Polyethylene Corporation); and an outer layer with a cross-sectional thickness of 0.100 mm that was composed of a mixture with a Shore hardness of 30D of polyurethane with a Shore hardness of 30D and SIBS.

Cylindrical member with an outer diameter of 0.70 mm was formed from a mixture of polyurethane with a Shore hardness of 30D and SIBS using an extruder.

The 40-mm two-layer tubes were arranged as tubular members on both sides. Then, the 25-mm cylindrical member was set as an intermediate connection member. The mixed materials in the tubular members and the connection member were welded together. After that, the tips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the both ends, thereby completing a lacrimal duct tube as shown in FIG. 5.

Example 5

Two-layer tubes with an outer diameter of 1.35 mm and an inner diameter of 0.95 mm were formed by multi-layer extrusion using an extruder such that a layer structure included: an inner layer with a cross-sectional thickness of 0.080 mm that was composed of polyamide elastomer with a Shore hardness of 63D (Pebax (registered trademark) 6333 produced by Arkema Inc.); and an outer layer with a cross-sectional thickness of 0.120 mm that was composed of polyamide elastomer with a Shore hardness of 25D (Pebax (registered trademark) 2533 produced by Arkema Inc.).

Cylindrical member with an outer diameter of 0.70 mm was formed from polyamide elastomer with a Shore hardness of 40D using an extruder.

The 40-mm two-layer tubes were arranged as tubular members on both sides. Then, the 25-mm cylindrical member was set as an intermediate connection member. The polyamide elastomers in the tubular members and the connection member were welded together. After that, the tips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the both ends, thereby completing a lacrimal duct tube as shown in FIG. 5.

Example 6

Three-layer tube with an outer diameter of 1.35 mm and an inner diameter of 0.95 mm was formed by multi-layer extrusion using an extruder such that a layer structure included: an inner layer with a cross-sectional thickness of 0.050 mm that was composed of a high-density polyethylene with a Shore hardness of 72D; an intermediate layer with a cross-sectional thickness of 0.010 mm that was composed of a low-density polyethylene with a Shore hardness of 50D; and an outer layer with a cross-sectional thickness of 0.140 mm that was composed of a mixture with a Shore hardness of 30D of polyurethane with a Shore hardness of 30D and SIBS.

Cylindrical member with an outer diameter of 1.35 mm and a cylindrical member with an outer diameter of 0.70 mm were formed from a mixture of polyurethane with a Shore hardness of 30D and SIBS using an extruder.

Tube with an outer diameter of 1.20 mm and an inner diameter of 0.95 mm was formed from high-density polyethylene with a Shore hardness of 72D using an extruder.

Then, 40-mm members were formed with a line structure in which mixed components in the 30-mm three-layer tube and the 10-mm cylindrical member with an outer diameter of 1.35 mm were welded together. The 40-mm members were arranged as tubular members on both sides such that the three-layer tube part was positioned at the tip side. Then, the 25-mm cylindrical member with an outer diameter of 0.70 mm was set as an intermediate connection member. The mixed materials in the tubular members and the connection member were welded together.

After that, tubes with an outer diameter of 1.20 mm and an inner diameter of 0.95 mm (composed of high-density polyethylene with a Shore hardness of 72D) were cut to a length of 2 mm and welded with tips of the high-density polyethylene portions (inner layer) in the tubular members to set the tube portions as end chips. The end chips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the end chips, thereby completing a lacrimal duct tube as shown in FIG. 6.

Example 7

Two-layer tubes with an outer diameter of 1.31 mm and an inner diameter of 0.95 mm were formed by multi-layer extrusion using an extruder such that a layer structure included: an inner layer with a cross-sectional thickness of 0.080 mm that was composed of nylon 12 with a Shore hardness of 72D; and an outer layer with a cross-sectional thickness of 0.100 mm that was composed of polyamide elastomer with a Shore hardness of 40D.

Cylindrical member with an outer diameter of 1.31 mm and a cylindrical member with an outer diameter of 0.70 mm were formed from polyamide elastomer with a Shore hardness of 40D using an extruder.

Tube with an outer diameter of 1.20 mm and an inner diameter of 0.95 mm was formed from nylon 12 with a Shore hardness of 72D using an extruder.

Then, 40-mm members were formed with a line structure in which the nylon 12 in the 30-mm two-layer tube and the polyamide elastomer (outer layer) in the 10-mm cylindrical member with an outer diameter of 1.31 mm were welded together. The 40-mm members were arranged as tubular members on both sides such that the two-layer tube part was positioned at the tip side. Then, the 25-mm cylindrical member with an outer diameter of 0.70 mm was set as an intermediate connection member. The polyamide elastomers in the tubular members and the connection member were welded together. After that, tubes with an outer diameter of 1.20 mm and an inner diameter of 0.95 mm were cut to a length of 2 mm and welded with tips of the nylon 12 portions (inner layer) in the tubular members to set the tube portions as end chips. The end chips of the tubular members were thermally compressed and bonded to core materials with an outer diameter of 0.86 mm using a shrink tube to reduce the inner diameters to 0.86 mm. In addition, holes were formed in the side surfaces of the tubular members at positions of 30 mm from the end chips, thereby completing a lacrimal duct tube as shown in FIG. 7.

Example 8

Tube with an outer diameter of 1.20 mm and an inner diameter of 0.95 mm was formed from nylon 12 with a Shore hardness of 72D using an extruder.

Cylindrical member with an outer diameter of 1.31 mm and a cylindrical member with an outer diameter of 0.70 mm were formed from polyamide elastomer with a Shore hardness of 40D using an extruder.

Then, 40-mm members were formed with a line structure in which the nylon 12 in the 30-mm tube and the polyamide elastomer in the 10-mm cylindrical member with an outer diameter of 1.31 mm were welded together. The 40-mm members were arranged as tubular members on both sides such that the nylon 12 tube was positioned at the tip side. Then, the 25-mm cylindrical member with an outer diameter of 0.70 mm was set as an intermediate connection member. The polyamide elastomers in the tubular members and the connection member were welded together. After that, the tips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the both ends, thereby completing a lacrimal duct tube as shown in FIG. 8.

Example 9

Tube with an outer diameter of 1.20 mm and an inner diameter of 0.95 mm was formed from nylon 12 with a Shore hardness of 72D using an extruder.

Tube with an outer diameter of 1.45 mm and an inner diameter of 1.30 mm were formed from polyamide elastomer with a Shore hardness of 40D using an extruder.

Cylindrical member with an outer diameter of 1.31 mm and a cylindrical member with an outer diameter of 0.70 mm were formed from polyamide elastomer with a Shore hardness of 40D using an extruder.

Spiral incision was made in the nylon 12 tube with an outer diameter of 1.20 mm and an inner diameter of 0.95 mm, and the nylon 12 tube was cut to a length of 30 mm. Then, the polyamide elastomer tube with an outer diameter of 1.45 mm and an inner diameter of 1.30 mm was placed on the nylon 12 tube, and a core material with an outer diameter of 0.95 mm was put into the inside of the tubes. The tubes were thermally compressed and welded together from the outside using a shrink tube, thereby completing a composite tube with an outer diameter of 1.30 mm and an inner diameter of 0.95 mm.

Then, 40-mm members were formed with a line structure in which the 30-mm composite tube and the polyamide elastomer in the 10-mm cylindrical member were welded together. The 40-mm members were arranged as tubular members on both sides such that the composite tube was positioned at the tip side. Then, the 25-mm cylindrical member with an outer diameter of 0.70 mm was set as an intermediate connection member. The polyamide elastomers in the tubular members and the connection member were welded together. After that, the tips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the both ends, thereby completing a lacrimal duct tube as shown in FIG. 9.

Example 10

A lacrimal duct tube as shown in FIG. 5 was produced in the same manner as that in the example 2 except that the inner layer was composed of nylon 12 with a Shore hardness 70D.

Comparative Example

Two-layer tubes with an outer diameter of 1.31 mm and an inner diameter of 0.95 mm were formed by multi-layer extrusion using an extruder such that a layer structure included: an inner layer with a cross-sectional thickness of 0.080 mm that was composed of polyamide elastomer with a Shore hardness of 55D (Pebax (registered trademark) 5533 produced by Arkema Inc.); and an outer layer with a cross-sectional thickness of 0.100 mm that was composed of polyamide elastomer with a Shore hardness of 40D.

Cylindrical member with an outer diameter of 0.70 mm were formed from polyamide elastomer with a Shore hardness of 40D using an extruder.

The 40-mm two-layer tubes were arranged as tubular members on both sides. Then, the 25-mm cylindrical member was set as an intermediate connection member. The polyamide elastomers in the tubular members and the connection member were welded together. After that, the tips of the tubular members were thermally compressed and bonded to core materials with an outer diameter of 0.86 mm using a shrink tube to form engagement portions (0.3 mm long) with an inner diameter reduced to 0.86 mm. In addition, holes were formed in the side surfaces of the tubular members at positions of 30 mm from the both ends, thereby completing a lacrimal duct tube as shown in FIG. 5.

Experimental Example

A silicon-based lacrimal duct model 13 was prepared with a nasolacrimal duct part 12 imitating the lacrimal duct as shown in FIG. 1. Each of the lacrimal duct tubes in the examples 1 to 10 and the comparative example was inserted into an evaluation circuit 15 having an imitated narrowed site 14 with an inner diameter of 0.9 mm (refer to FIG. 10) in the lacrimal duct model 13, by the use of a lacrimal endoscope having a probe of 0.9 mm in diameter (not shown) according to the sheath guided endoscopic probing, thereby to evaluate these lacrimal duct tubes for properties of retaining the viewing field of the endoscope, facilitating manipulation of the endoscope, and securing insertability into the narrowed site. The probe was covered with the lacrimal duct tube. Evaluation results are as shown in Table 1.

The evaluation for the property of retaining the endoscope viewing field was made on whether the viewing field of the endoscope was narrowed by deformation of the lacrimal duct tube (in particular, the tip portion).

The evaluation for the property of facilitating manipulation of the endoscope was made on whether resistance of the lacrimal duct tube to the endoscope was low, the two could be smoothly adjusted in position relative to each other, and the endoscope could be smoothly removed after passage through the lesion site.

The evaluation for the property of securing insertability into the narrowed site was made on whether the lacrimal duct tube could be smoothly inserted into the narrowed site.

As for the foregoing three properties, Table 1 shows one each of the following ratings for the lacrimal duct tubes provided by a majority of four testers:

S: Capable of extremely smooth operation without any problem.
A: Capable of smooth operation with very few problems.
B: Capable of acceptable operation with a few problems.
C: Extremely difficult to operate with severe problems.

From the results shown in Table 1, it is found that all the lacrimal duct tubes in the examples 1 to 10 were rated within a range "S" to "B" at all of the evaluations.

The lacrimal duct tube in the example 6 is the same in structure as the lacrimal duct tube in the example 1 except that the outer diameter of the tube tip is smaller. However, the lacrimal duct tube in the example 6 is further improved in insertability into the narrowed site as compared to the one in the example 1.

Similarly, the lacrimal duct tube in the example 7 is smaller in the outer diameter of the tube tips than that of the lacrimal duct tube in the example 2, and is further improved in insertability into the narrowed site.

The lacrimal duct tube in the example 8 has tips harder than base ends to improve insertability into the narrowed site.

The lacrimal duct tube in the example 9 has a spiral incision in the inner layer and thus is further improved in facilitating manipulation of the endoscope and securing insertability into the narrowed site as compared to the lacrimal duct tube in the example 2.

The lacrimal duct tubes in the examples 1 to 7 have a layer structure as shown in FIGS. 5 to 7 and have a difference in Shore hardness between the inner layer and the outer layer adjusted to 16D or more. Accordingly, these lacrimal duct tubes are favorable in the properties of retaining the viewing field of the endoscope, facilitating manipulation of the endoscope, and securing insertability into the narrowed site.

The lacrimal duct tube in the example 8 has a line structure as shown in FIG. 8 and has a difference in Shore hardness between the opening-side resin portion and the hole-side resin portion adjusted to 16D or more. Accordingly, the lacrimal duct tube in the example 8 is favorable in the properties of retaining the viewing field of the endoscope, facilitating manipulation of the endoscope, and securing insertability into the narrowed site.

Meanwhile, the lacrimal duct tube in the comparative example was rated as "C" for the property of retaining the viewing field of the endoscope because the tips of the tube deformed at the bent site or the narrowed site, hung over the endoscope, and significantly limited the viewing field of the endoscope.

In addition, the lacrimal duct tube in the comparative example was rated as "C" for the property of facilitating manipulation of the endoscope because a considerable friction occurred between the endoscope and the lacrimal duct tube at the bent site and the narrowed site to make it difficult to adjust the relative positions of the endoscope and the lacrimal duct tube, and the endoscope was extremely hard to remove.

Further, the lacrimal duct tube in the comparative example was rated as "C" for the property of securing insertability into the narrowed site because a considerable friction occurred between the tip of the lacrimal duct tube and the narrowed site, and when an attempt was made to insert the tip of the lacrimal duct tube, the tip turned and deformed and thus was hard to insert.

TABLE 1

| | Retention of viewing field of endoscope | Manipulation of endoscope | Insertability into narrowed site |
|---|---|---|---|
| Example 1 | A | A | A |
| Example 2 | A | A | A |
| Example 3 | A | A | A |
| Example 4 | B | B | B |
| Example 5 | B | B | B |
| Example 6 | A | A | S |
| Example 7 | A | A | S |
| Example 8 | A | B | S |
| Example 9 | A | S | S |
| Example 10 | A | A | A |
| Comparative Example | C | C | C |

REFERENCE SIGNS LIST

1 Lacrimal duct tube
2 Opening
3 Hole
4 Tubular member
5 Connection member
6 Bar-like operative instrument
7 Resin portion
8 Lumen
9 Lumen wall
10 Engagement portion
11 Tubular member
12 Nasolacrimal duct part
13 Lacrimal duct model
14 Imitated narrowed site
15 Evaluation circuit
16 Spiral incision
21 Upper lacrimal punctum
22 Lower lacrimal punctum
23 Upper lacrimal canaliculus
24 Lower lacrimal canaliculus
25 Common canaliculus
26 Lacrimal sac
27 Nasolacrimal duct
28 Inferior nasal meatus
29 Lacrimal endoscope
30 Sheath
31 Lacrimal duct
32 Obstructed site
33 Lacrimal duct tube
X Thickness direction
Y Longitudinal direction

The invention claimed is:

1. A lacrimal duct tube, comprising:
a pair of tubular members that each has an opening at one end and a hole in a side wall communicating with a lumen having a lumen wall; and
a connection member that connects other ends of the tubular members, wherein
the tubular members each comprises a plurality of resin portions different in Shore hardness,
at least one of the resin portions is positioned between the opening and the hole and forms a lumen wall of the tubular member comprises, and
the lumen wall has a Shore hardness of 57D or more between the opening and the hole of the tubular member.

2. The lacrimal duct tube according to claim 1, wherein the plurality of resin portions has:
a line structure in which the resin portions are aligned along a longitudinal direction of the tubular member so that the lumen wall has a Shore hardness of 57D or more between the opening and the hole of the tubular member;
a layer structure in which the resin portions are aligned along a thickness direction of the tubular member so that the lumen wall has a Shore hardness of 57D or more between the opening and the hole of the tubular member; or
a mixed structure of the line structure and the layer structure.

3. The lacrimal duct tube according to claim 2, wherein the layer structure includes at least one set of layers in which an inner resin portion is higher in hardness than an outer resin portion.

4. The lacrimal duct tube according to claim 3, wherein, in the layer structure, the difference in Shore hardness between the inner resin portion and the outer resin portion is 16D or more.

5. The lacrimal duct tube according to claim 3 or 4, wherein, in the layer structure, an innermost resin portion is higher in hardness than the other resin portions.

6. The lacrimal duct tube according to claim 2 wherein the line structure includes at least one set of lines in which a resin portion on the opening side is higher in hardness than a resin portion on the hole side.

7. The lacrimal duct tube according to claim 6, wherein, in the line structure, the difference in Shore hardness between the resin portion on the opening side and the resin portion on the hole side is 16D or more.

8. The lacrimal duct tube according to claim 6 or 7, wherein, in the line structure, a resin portion nearest the opening side is higher in hardness than the other resin portions.

9. The lacrimal duct tube according to claim 2, wherein, in the layer structure, the outermost resin portion is formed from polyamide elastomer or a mixed material of polyurethane and styrene-isobutylene-styrene block copolymer (SIBS).

10. The lacrimal duct tube according to claim 1, wherein the hole is an inlet for an operating bar or a lacrimal endoscope as a bar-like operative instrument of the lacrimal duct tube.

11. The lacrimal duct tube according to claim 10, wherein the lumen wall in the vicinity of the opening has an engagement portion for engagement with a tip of the bar-like operative instrument housed in the lumen through the hole.

12. The lacrimal duct tube according to claim 11, wherein the engagement portion forms the diameter of the lumen of the tubular member so as to be smaller than the outer diameter of the tip of the bar-like operative instrument.

13. The lacrimal duct tube according to claim 1, wherein the resin portion having the lumen wall with a Shore hardness of 57D or more is formed from polyamide or polyethylene.

14. The lacrimal duct tube according to claim 1, wherein the lumen wall comprises at least one of the resin portions in a spiral to form a continuous inner surface in a longitudinal direction.

* * * * *